(12) United States Patent
Fillières et al.

(10) Patent No.: US 11,439,160 B2
(45) Date of Patent: Sep. 13, 2022

(54) METHOD FOR PRODUCING HYDROLYSED KERATINACEOUS MATERIAL

(71) Applicant: TESSENDERLO CHEMIE N.V., Brussels (BE)

(72) Inventors: Romain Fillières, Vernon (FR); Marc Belmans, Tessenderlo (BE); Frank Boers, Tessenderlo (BE); Faye Maertens, Schaffen (BE); Joeri Rogiers, Zolder (BE)

(73) Assignee: Tessenderlo Chemie N.V., Brussels (BE)

( * ) Notice: Subject to any disclaimer, the term of this patent is extended or adjusted under 35 U.S.C. 154(b) by 782 days.

(21) Appl. No.: 14/908,564

(22) PCT Filed: Jul. 29, 2014

(86) PCT No.: PCT/EP2014/066313
§ 371 (c)(1),
(2) Date: Jan. 29, 2016

(87) PCT Pub. No.: WO2015/014859
PCT Pub. Date: Feb. 5, 2015

(65) Prior Publication Data
US 2016/0157511 A1    Jun. 9, 2016

Related U.S. Application Data

(60) Provisional application No. 61/881,534, filed on Sep. 24, 2013.

(30) Foreign Application Priority Data

Jul. 30, 2013   (EP) .................................... 13178526

(51) Int. Cl.
| | | |
|---|---|---|
| *A23J 3/32* | (2006.01) |
| *A23J 1/10* | (2006.01) |
| *A23L 33/18* | (2016.01) |
| *C08H 1/06* | (2006.01) |
| *A23J 3/30* | (2006.01) |
| *A61K 8/65* | (2006.01) |
| *A61Q 19/00* | (2006.01) |

(52) U.S. Cl.
CPC . *A23J 3/32* (2013.01); *A23J 1/10* (2013.01); *A23J 3/30* (2013.01); *A23L 33/18* (2016.08); *A61K 8/65* (2013.01); *A61Q 19/00* (2013.01); *C08H 1/06* (2013.01); *A23V 2002/00* (2013.01); *A61K 2800/10* (2013.01)

(58) Field of Classification Search
CPC ........ A23J 3/32; A23J 1/10; A23J 3/30; A23J 3/341; A23L 33/18; A61K 8/65; A61K 2800/10; A61K 38/015; A61Q 19/00; C08H 1/06; A23V 2002/00
See application file for complete search history.

(56) References Cited

U.S. PATENT DOCUMENTS

| | | | |
|---|---|---|---|
| 2,542,984 A | 2/1951 | Binkley | |
| 2,702,245 A | 2/1955 | Klein et al. | |
| 3,006,809 A | 10/1961 | Gershon | |
| 3,806,501 A * | 4/1974 | Rymer et al. ............. | A23J 1/10 |
| | | | 530/357 |
| 4,172,073 A | 10/1979 | Kadri et al. | |
| 4,269,865 A | 5/1981 | Retrum | |
| 4,286,884 A | 9/1981 | Retrum | |
| 4,591,497 A | 5/1986 | Naito et al. | |
| 4,818,520 A | 4/1989 | Jaskiewicz | |
| 4,874,893 A * | 10/1989 | Flork .................... | C07C 227/28 |
| | | | 562/443 |
| 5,049,397 A | 9/1991 | Kolbeck et al. | |

(Continued)

FOREIGN PATENT DOCUMENTS

| | | |
|---|---|---|
| CN | 101874545 A | 11/2010 |
| CN | 102191305 A | 9/2011 |
| CN | 102911994 A | 2/2013 |

(Continued)

OTHER PUBLICATIONS

Taskin et al., International Journal of Food Sciences and Nutrition, Aug. 2012; 63(5): 597-602.*

(Continued)

*Primary Examiner* — Lianko G Garyu
(74) *Attorney, Agent, or Firm* — David Owen; Hoyng Rokh Monegier

(57) ABSTRACT

The method of the invention comprises the production of highly digestible hydrolysed keratinaceous material comprising the steps of (i) partly hydrolysing keratinaceous material with heat and pressure and (ii) optionally drying the resultant partly hydrolysed material comprising at least partly insoluble material and (iii) subjecting the optionally dried partly hydrolysed keratinaceous material to a chemical hydrolysis step with acid or base to obtain a highly digestible hydrolysed material, and (iv) purifying the highly digestible material. The invention further provides highly digestible keratinaceous material with an amino acid composition reflecting the amino acid composition of the raw material, wherein the amount of de-carboxylated amino acids is less than 500 ppm. Preferably all of the highly digestible material has a molecular weight lower than 10000 dalton, and preferably more than 95 wt % of the highly digestible keratinaceous material has a molecular weight of less than 5000 dalton.

14 Claims, No Drawings

(56) References Cited

U.S. PATENT DOCUMENTS

| | | | |
|---|---|---|---|
| 5,262,307 A | 11/1993 | Savolainen | |
| 5,772,968 A | 6/1998 | Wolfe | |

FOREIGN PATENT DOCUMENTS

| | | | |
|---|---|---|---|
| EP | 1021958 A1 | 7/2000 | |
| EP | 1566482 A1 | 8/2005 | |
| FR | 2448297 A1 | 9/1980 | |
| GB | 2061956 A | 5/1981 | |
| RU | 2206231 C2 | 6/2003 | |
| WO | 8705895 A1 | 10/1987 | |
| WO | 9216113 A1 | 10/1992 | |
| WO | 9837773 A1 | 9/1998 | |
| WO | 2010114938 A1 | 10/2010 | |
| WO | 2011/003015 A1 | 1/2011 | |

OTHER PUBLICATIONS

Processing of Poultry Byproducts and Their Utilization in Feeds, Nov. 1961, US Government Printing Office.*
Regulation (EC) No. 1069/2009 of the European Parliament and of the Council of Oct. 21, 2009, 33 pages.*
Processing of Poultry Byproducts and Their Utilization in Feeds, Nov. 1961, US Government Printing Office (Year: 1961).*
Regulation (EC) No. 1069/2009 of the European Parliament and of the Council of Oct. 21, 2009, 33 pages (Year: 2009).*
Taskin et al., Eur Food Res Technol (2011) 233:657-665 (Year: 2011).*
Autoclave Temperature and Time Pressure Chart, from JADA, vol. 122, 1991 (Year: 1991).*
Priority Search Report for EP2832237 dated Jan. 29, 2014.
International Search Report for PCT/EP2014/066313 dated Nov. 17, 2015.
International Preliminary Report on Patentability for PCT/EP2014/066313 dated Feb. 2, 2016.
Kim et al, Effect of Enzymatic and Chemical Treatments on Feather Solubility and Digesttibility, 2002, Poultry Science, vol. 81 : 95-98.
Kumar Et Al, Production of Feather Protein Concentrate from Feathers by In vitro Enzymatic Treatment, its Biochemical Characterization and Antioxidant Nature, 2012, Middle-East Journal of Scientific Research, vol. 11 (7): 881-886.
Eggum et al, Evaluation of Protein Quality of Feather Meal Under Different Treatments, 1970, Acta Agriculture Scandinavia, vol. 20 : 230-234.
Kim et al, Nutritional Value of Enzyme- or Sodium Hydroxide-Treated Feathers from Dead Hens, 2000, Poultry Science, vol. 79 : 528-534.
Latshaw, Quality of Feather Meal as Affected by Feather Processing Conditions, 1990, Poultry Science, vol. 69: 953-958.
Steiner et al, Effect of Sodium Hydroxide and Phosphoric Acid Treatment on Pepsin and in Vitro Digestibilities of Steam Hydrolyzed Feather Meal, 1981, Proceedings, Western Section, American Society of Animal Science, vol. 32, 56-59.
Journal Officiel De L'Union Europeenne, Reglement UE, Feb. 25, 2011, No. 142/2011, pp. 1-21 and 27-32.
AOAC International, 4.4.04 Method for Measuring Pepsin Digestibility of Animal Proteins Feeds, method 1971-1973, published 2012.
Piazza et al., Proteins and peptides as renewable flocculants, Biosource Technology 101, (2010) 5759-5766, Elsevier ltd, doi: 10.1016/j.biortech.2010.02.073.
Moran et al., Keratins as source of Protein for the Growing Chick, Aug. 29, 1966, Departments of Poultry Science and Nutrition, University of Guelph, Guelph, Ontario, Canada.
Leaflet Kerapro, a hydrolysed Feather Protein in Pet Food, SONAC, Jan. 2011.

* cited by examiner

METHOD FOR PRODUCING HYDROLYSED KERATINACEOUS MATERIAL

CROSS REFERENCE TO RELATED APPLICATIONS

This application is a 35 U.S.C. 371 National Stage of PCT application number PCT/EP2014/066313 filed on 29 Jul. 2014, which claims priority from EP application number 13178526.3 filed on 30 Jul. 2013 and from U.S. application No. 61/881,534 filed on 24 Sep. 2013. All applications are hereby incorporated by reference in their entireties.

BACKGROUND OF THE INVENTION

1. Field of the Invention

The invention relates generally to a method for producing hydrolysed keratinaceous material.

2. Description of the Related Art

As a source of keratinaceous material, animal feathers, hair, hoof, nails and the like can be used. Feathers are by-products from poultry (chicken, turkey, duck and the like), and hair is a by-product from pigs, cattle, sheep and the like. Also hoofs or nails, that may be grinded, can be used as source of keratinaceous material. Such keratinaceous material has a high protein content (generally more than 80 wt % of the dry substance is protein), comprising at least 17 amino acids. However, this raw keratinaceous material is hardly digestible for animals or humans because of the presence of many (di)sulphide bridges in highly structured polypeptides.

Many processes exist for producing partly hydrolysed keratinaceous material like feathers or hair, in order to increase the digestibility. Known methods include hydrolysis under pressure while using steam, oxidation with hydrogen peroxide, reduction with sulphites, enzymatic hydrolysis and chemical hydrolysis with base or acid.

The keratinaceous material is generally hydrolysed only to a certain extent. These processes comprise a.o. chemical hydrolysis or steam hydrolysis. In case the products have substantial amounts of high molecular weight keratinaceous polypeptides, the digestibility is limited, and such products comprise potentially allergenic compounds because of the high molecular weight (about 18000 or higher). Keratinaceous material which is hydrolysed to an extent that it is fully digestible generally requires harsh conditions, with strong acids or base in substantial excess. This causes, apart from large waste streams, often also degradation (like de-amination; de-carboxylation) of some of the amino acids, which eventually lowers the digestibility.

Several examples of methods for producing partly hydrolysed feather meal are included in the following documents U.S. Pat. Nos. 2,542,984, 5,049,397, RU2206231, U.S. Pat. Nos. 5,772,968, 4,286,884, 4,172,073, WO2010/114938, U.S. Pat. No. 3,806,501, EP1566482, GB2061956 and WO2011/003015.

BRIEF SUMMARY OF THE INVENTION

It is an object of the invention to provide a method for producing hydrolysed keratinaceous material with a very high digestibility, and which preferably consists of peptides of relatively low molecular weight while having high nutritional value.

This object is achieved by the method of the invention for the production of highly digestible hydrolysed keratinaceous material comprising the steps of (i) partly hydrolysing keratinaceous material in the presence of water with heat and pressure and optionally steam; and (ii) optionally drying the resultant partly hydrolysed material comprising at least partly insoluble material; and (iii) subjecting the optionally dried partly hydrolysed keratinaceous material to a chemical hydrolysis step with acid or base to obtain a highly digestible hydrolysed material, and (iv) purifying the highly digestible material.

Preferably, a sufficient amount of acid or base is used, while performing the reaction for a sufficient time and at a sufficiently high temperature to obtain a highly digestible hydrolysed material that has about 95% by weight or more of peptides of a molecular weight of about 5000 dalton or less. This is an advantage, as keratinaceous material with a molecular weight of about 5000 dalton or lower is considered hypo-allergenic, whereas material with a molecular weight of about 18000 dalton or higher is considered by some to be responsible for food intolerance to dogs and cats subject to allergenic problems.

In the present invention, a relatively low molecular weight preferably means that about 97% has a molecular weight lower than 10000 dalton, and more than about 95 wt % of the hydrolysed keratinaceous material has a molecular weight of about 5000 dalton or less. Preferably, practically all the material has a molecular weight of about 10000 dalton or less.

It is furthermore particularly preferred, that the hydrolysed keratinaceous material has for 95% or more a molecular weight of about 3000 dalton or less, and even more preferred 90% or more a molecular weight of about 1000 dalton or less, as such polypeptides are considered an-allergenic.

It is particularly preferred to obtain a material that has typically all the material of a molecular weight of about 5000 dalton or less and about 95% or more of a molecular weight of about 1000 dalton or less. Lower molecular weights are also preferred, as these improve the digestibility.

It is a further object of the invention to provide a highly digestible hydrolysed keratinaceous material with an improved nutritional value for feed applications.

This object is achieved by providing partly or fully soluble keratinaceous material with an amino acid composition reflecting the amino acid composition of the raw material, wherein the amount of de-carboxylated amino acids is about 1000 ppm or less, preferably about 500 ppm or less, and most preferably about 300 ppm or less.

The highly digestible material preferably is fully soluble, which means that 1 gram of a hydrolysed keratinaceous material is soluble in 5 ml of water.

The molecular weights of this keratinaceous material according to the invention are preferably as described above.

As it is clear from the molecular weights, the hydrolysis is not a complete chemical hydrolysis to mono-amino acids, but the hydrolysis comprises the hydrolysation of a substantial number of amide bonds in the polypeptides.

The presence of water during the hydrolysation step is meant to be any of liquid phase water, steam, or water absorbed in the keratinaceous material.

In this description, an amino acid composition reflecting the amino acid composition of the raw material preferably means that the deviation in amino acid composition is less than 20% in any of the amino acids, and/or a deviation in an amount absolute of less than 0.4 wt % in most amino acids, whereby a small number of amino acids—like 2 or 3—may deviate more, like for example to a maximum of 40% or 2 wt %.

It appeared that the harsh conditions of the chemical hydrolysis disclosed in the prior art caused de-carboxylation, in particular of amino acids with amino-group bearing side chains such as lysine or deamination of the side chains. These de-carboxylated or de-aminated amino acids can be toxic or anti-nutritional.

Cysteine is generally present as cystine. Cystine (the disulphide dimer of cysteine) is digestible, and generally HPLC methods do not distinguish between these two forms. In this application, cysteine is used, although the actual form may be cystine.

A number of chemical hydrolysis methods oxidize the cystine residues, which limits the amount of available cysteine.

Other reaction products of the amino acids may have anti-nutritional value (i.e. they reduce the effect of the feed ingredient). The amount of amino-acid derivatives with anti-nutritional value (such as lanthionine or lysinoalanine) preferably is low. The amount of lanthionine preferably is about 2.5 wt % or lower, preferably about 2 wt % or lower, and even more preferable about 1.5 wt % or lower. The amount of cysteine is preferably about 3 wt % or more, and even more preferably about 4 wt % or more.

The process of the present invention allows the production of partly or fully solubilized keratinaceous material with high nutritional value, because of very low amounts of toxic or anti-nutritional amino-acid derivatives.

It is an advantage of the process of the present invention, that a majority of the keratinaceous starting material is converted to low molecular weight products. Hence, a product is recovered having relatively low molecular weight. Yields are preferably about 80% or higher (weight fed vs weight obtained, assuming about the same moisture content), and more preferable about 85% or higher. The material fed into step (iii) does contain fat, ashes and other non-keratinaceous materials that cannot yield highly digestible keratinaceous material.

In the method according to the invention, the chemical hydrolysis step preferably is performed with a strong mineral acid like hydrochloric acid, phosphoric acid or sulphuric acid. In case a strong base is used, preferably sodium hydroxide, potassium hydroxide, calcium oxide or calcium hydroxide or the like are used.

The purification of the highly digestible hydrolysed keratinaceous material is preferably performed while forming a salt by neutralisation and separating the salt from the keratinaceous material. The neutralization step can be done by adding the acid solution to the base solution, or the other way around. Separating the base, acid or salt does not have to be a complete removal, as some residual salt and/or ions are acceptable. Residual amounts of salts of up to 10-20% may be acceptable, although an amount of about 7 wt % or less is preferred.

The purification step may not always be necessary, if the use allows the presence of a relatively high amount of salt. Hence, in certain embodiments, the result of the neutralized hydrolysed reaction mixture may be used as such, in particular in pre-mixes with other nutrients.

Preferably, the salt is an insoluble salt, preferably calcium sulphate dihydrate, which is removed by filtration or centrifugation.

Hence, in a preferred embodiment, the hydrolysis is performed with sulphuric acid and the purification is effected by neutralizing the acid with a calcium base, and removing the formed calcium sulphate dihydrate precipitate.

No other purification steps are necessary, although further steps are not excluded. Preferably, the purification comprises the removal of acid, base or salt as the only purification step. After this purification step, a concentration and/or drying step is performed, which also will cause an amount of volatile organic compounds to be removed. The removal of organic volatiles is not considered in practice to be a purification step.

In one preferred embodiment, the hydrolysed keratinaceous material is concentrated to a solution of about 10 wt % or more solid matter, preferably about 30-60 wt % of solid matter, and more preferably about 40-55 wt % solid matter. Such concentrated liquid hydrolysed keratinaceous material can be used as such.

In a further preferred embodiment of the invention, the purified hydrolysed keratinaceous material is dried in a hot air flow, like for example a hot air drum dryer, a fluidized bed dryer and any other mild drying systems, preferably a spray dryer. Generally, a concentrated liquid hydrolysed keratinaceous material as described above is used as starting material for the drying step.

In a preferred embodiment, the ash content of the dry highly digestible keratinaceous material preferably is about 15 wt % or less, more preferably about 10 wt % or less, and most preferred, about 8 wt % or less. Generally, the ash content will be about 2 wt % or higher. The concentrated liquid preferably has an equivalent amount of ash content (relative to dry matter).

In a preferred embodiment, the partly hydrolysed keratinaceous material obtained after step (ii) has an amount of lanthionine of about 2 wt % or less, preferably about 1.5 wt % or less, and most preferably about 0.5 wt % or less.

In a preferred embodiment, the hydrolysed, fully soluble keratinaceous material has an amount of cadaverine (decarboxylated lysine/Lys), putrescine (decarboxylated ornithine) and/or histamine (decarboxylated histidine/His); individually of less than about 500 ppm, preferably less than about 300 ppm and most preferably less than about 100 ppm. Furthermore, or in the alternative, the total amount of these amines is present in an amount of less than about 1000 ppm, preferably less than about 500 ppm, more preferably less than about 300 ppm. Furthermore, it is particularly preferable, that the material contains also an amount of lanthionine of less than 1.5 wt %, preferably less than 1.0 wt %.

The amino acid composition of the highly digestible keratinaceous material (hydrolysate) according to the invention preferably is approximately as defined in table 1 (amounts in wt %):

| Amino acid | Initial Amount Total amino acids in feather meal | Amount Total amino acids in hydrolysate |
| --- | --- | --- |
| Asp | 6.7 | 6.6 |
| Thr | 4.8 | 4.6 |
| Ser | 12.1 | 10.8 |
| Glu | 10.4 | 10.8 |
| Pro | 11.0 | 10.0 |
| Gly | 7.8 | 7.6 |
| Ala | 4.6 | 4.9 |
| Val | 7.6 | 8.3 |
| Cys | 4.7 | 4.8 |
| Met | 0.5 | 0.6 |
| Ile | 4.9 | 5.2 |
| Leu | 8.1 | 8.9 |
| Tyr | 2.3 | 2.0 |

-continued

| Amino acid | Initial Amount Total amino acids in feather meal | Amount Total amino acids in hydrolysate |
|---|---|---|
| Phe | 5.2 | 5.2 |
| Lys | 1.7 | 2.0 |
| His | 0.7 | 0.8 |
| Arg | 6.9 | 7.0 |
| Total | 100% | 100% | whereby the amount of cadaverine is less than about 500 ppm, preferably less than about 300 ppm, and more preferably less than about 100 ppm. Furthermore, the total of biogenic amines (i.e. for example putrescine, cadaverine and histamine) is preferably less than about 1000 ppm, more preferably less than 500 ppm, and most preferable less than 300 ppm.

Preferably, this composition is combined with the feature that the amount of lanthionine is less than 1.5 wt %.

In another embodiment of this invention, the invention relates to a method for the production of highly digestible hydrolysed keratinaceous material comprising the steps of subjecting directly raw feathers, hair, wool, hoof or nails to a chemical hydrolysis step (iii) with acid or base to obtain a highly digestible hydrolysed material, and (iv) purifying the highly digestible hydrolysed material, preferably using any one of the preferences described herein.

In a preferred embodiment, several or all preferences are combined, as also appears from several of the examples.

DESCRIPTION OF ILLUSTRATIVE EMBODIMENTS

The following is a description of certain embodiments of the invention, given by way of example only and with reference to the examples.

The method of the invention for the production of highly digestible hydrolysed keratinaceous material—as described—comprises the steps of (i) partly hydrolyzing keratinaceous material in the presence of water with heat and pressure and (ii) optionally drying the resultant partly hydrolysed material comprising at least partly insoluble material and (iii) subjecting the optionally dried partly hydrolysed keratinaceous material to a chemical hydrolysis step with acid or base to obtain a highly digestible hydrolysed material, and (iv) purifying the highly digestible material.

The keratinaceous material used in the present invention preferably comprises feathers, hair, wool, hoof or nails. Feathers are by-products from poultry (chicken, turkey, duck and the like), and hair and wool is a by-product from pigs, cattle, sheep and the like. Hoof or nails can originate from a variety of animal sources and may be used in grinded form as source of keratinaceous material.

In a preferred embodiment, feathers are used as keratinaceous material as that is continuously available in substantial amounts, such that an industrial plant can be on stream continuously.

The keratinaceous material for use in the present invention preferably has a high protein content (generally more than 80 wt % of the dry substance), comprising at least 17 amino acids. The protein content normally is determined by measuring the total amount of nitrogen, and multiplying said total nitrogen content with the so-called Jones factor of 6.25. The result is the theoretical amount of protein. Generally, feathers comprise between 70-90% protein on solids; the amount of solids in raw feathers collected from a slaughterhouse generally is about 30 wt %. Feather meal generally contains about 72 to about 87 wt % protein, assuming less than 8 wt % moisture.

The partial hydrolysis of the keratinaceous material in step (i) of the process of the invention, in a preferred process will be the following: (a) loading of a continuous or discontinuous hydrolyzer with raw feathers or other keratinaceous material (raw feathers have e.g. between 55% and 70% moisture; which moisture generally comes from the slaughterhouse as the birds are scalded in hot water before plucking, plucked feathers are then conveyed in water to a centrifuge or press before discharge in the receiving bin), (b) heating up of the hydrolyzer by means of steam jackets (and/or injection of direct steam), pressure build up due to water evaporation, maintaining pressure at about 2 bar to about 15 bar, preferably between 2 to 8 bars during 10 to 30 min, (c) depressurizing and discharging to a drying section.

The keratinaceous material may be milled or crushed to reduce the size before loading in the hydrolyser. Generally, size reduction for feathers and hair of pigs or cattle is not very useful.

The wet keratinaceous material generally will have a moisture content of between about 30 and about 80% (% moisture relative to the total weight of the keratinaceous material plus moisture) when supplied to the hydrolyser, preferably the moisture content is about 50 wt % or more, and commonly around about 70%. It is preferred to use less than 75 wt % of moisture (i.e. less than 3 parts water on 1 part of dry substance keratinaceous material), because the added water needs to be removed, and takes energy to heat in the hydrolyser. Therefore, a preferred amount of water is about 65 wt % or less (at most about 2 parts of water relative to 1 part of dry substance of keratinaceous material, preferably feathers).

The hydrolyser generally works at a pressure of about 15 bar or lower, preferably 10 bar or lower, as higher pressure is increasingly costly. The pressure generally is about 2 bar or higher. Higher pressure is preferred to increase the degree and speed of hydrolysation. Hence, the pressure preferably is about 4 bar or higher, and even more preferable, about 6 bar or higher. Generally, the pressure will be about 9 bar or lower. The pressure is given as bar absolute.

The hydrolysis reaction is breaking up peptide bonds by the action of steam at the temperature which depends on the pressure. Hence, generally, no acid or base is present, unless accidentally coming from the slaughterhouse. Although small amounts of added reagents are possible to use, it is preferred to have a hydrolysis reaction with only water/steam as the active reagent.

The hydrolysis in step (i) will be performed in a hydrolyser, which is generally called a steam-hydrolyser. Such hydrolyser is essentially a stirred vessel, and may be operated as a batch or continuous process. The hydrolyser preferably allows a continuous process, and is a stirred tube like vessel, like an extruder or a vertical stirred vessel. Stirring preferably is done with a slowly propelling screw type of mixer, paddles or the like.

The hydrolysis step (i) generally will last between about 5 and about 240 min, preferably between about 10 and about 180 min. Lower pressure generally requires longer reaction times. It is preferred to perform the reaction in such a way, that the residence time in the hydrolyser will be about 60 min or less, most preferred about 40 min or less.

The steam may be directly injected, or may be used for indirect heating. Indirect heating may also be affected with e.g. hot oil coils. Ultimately, the pressure should be as required, and the amount of water preferably is such, that saturated steam is present at the chosen pressure and temperature. Preferably, the amount of steam present is about 200 gram of steam or more per kg of keratinaceous material.

The partly hydrolysed keratinaceous material will be optionally dried hereafter according to step (ii) of the present invention. This drying generally is done in a number of steps. The first step comprises bringing the mixture leaving the steam-hydrolyser to atmospheric pressure, while evaporating part of the water. This water is condensed, and treated in a waste water treatment, oxidised or the like.

Optionally, it is possible to press part of the water from the keratinaceous material to bring the water content from, for example, about 65 wt % to about 45 wt %.

In one embodiment of the invention, the resultant, still moist partly hydrolysed keratinaceous material is dried to a moisture content of about 10 wt % or less, preferably about 8 wt % or less. Drying to an amount of water lower than 4 wt % generally is not necessary, but would not harm. Drying is most preferably performed till a moisture content of about 5-7 wt %. Drying results in a storage stable product. Thus, in this preferred embodiment, the partly hydrolysed keratinaceous material is further used as a dry product, with a moisture content of about 10 wt % or less.

In case the further hydrolysis step with acid or base is performed shortly after the first partial hydrolysis, it is not necessary to dry the partly hydrolysed keratinaceous material. A moisture content of about 40 to about 60 wt % is suitable. Hence, in another preferred embodiment, the chemical hydrolysis step is performed on partly steam-hydrolysed keratinaceous material wherein the moisture content of the partly hydrolysed keratinaceous material has not been lower than 25 wt % water, and is about 45 wt % or more. This has the advantage, that less energy is necessary and that deterioration caused by the heating step is prevented.

Drying can be done with conventional methods such as disc drying, hot air drying (in a fluidized bed dryer, ring dryer or the like) and the like.

An advantage of providing dried partly hydrolysed and partly soluble keratinaceous material is, that this intermediate feedstock is storage stable. Furthermore, providing such intermediate feedstock increases flexibility, as this keratinaceous material may be useful for other applications than the further chemical hydrolysis according to the present invention.

In one embodiment of the invention, the drying of step (ii) is performed at reduced pressure. Suitable pressure include a pressure below 0.4 bar (abs), preferably below 0.3 bar. At a pressure of 0.3 bar, water boils at about 70° C., and thereby the keratinaceous material largely remains at a temperature below such temperature. An even lower vacuum is also possible, but may have the disadvantage that such low vacuum is relatively expensive to keep. Hence, the reduced pressure generally will be a pressure higher than 10 mbar abs. Higher temperatures can be used, if the residence time is shortened. In a fluidized bed dryer, good results were obtained as well.

In order to allow an economical process, it is important that the plant for treating the keratinaceous material is able to process about 2 ton per hour or more, preferably between 4 and 15 tonnes per hour.

Drying appears to be an important step in the quality of the keratinaceous material such as feather meal. It appears that common drying techniques cause the digestibility to be reduced, although any resulting feather meal can still be used in the further chemical hydrolysis process.

By drying at relatively low temperature, it is possible to obtain partly hydrolysed, insoluble keratinaceous material with a moisture content of less than 8 wt % and a lanthionine content of less than 2 wt %, preferably less than 1 wt %. In one preferred embodiment, the partly hydrolysed material resulting from step (i) is dried with a method allowing low heat damage, such that the reduction in digestible material is such, that the pepsin and/or ileal digestibility is still higher than 90%. More preferably, the reduction in pepsin and/or ileal digestibility measured before and after the drying step is preferably less than 5%.

The partly hydrolysed material obtained from step (ii) is at least partly insoluble in water, when 1 gram is put in 5 ml of water particles are seen with the eye. Nevertheless, it is possible to measure the molecular weight distribution of at least part of the keratinaceous material. The most commonly used method is HPLC with water, optionally with acetonitrile, and trifluoroacetic acid (TFA; 0.1%) as a solvent and a normal SEC as a column. Calibration can e.g. be done with proteins. The partly hydrolysed material shows a broad peak. The molecular weight distribution is in this field often not denoted as Mn/Mw, as not all material may be dissolved. It is possible to state which part of the material measured in the HPLC has a certain molecular weight.

In a preferred embodiment of the invention, the partly hydrolysed keratinaceous material comprises—when dissolved in water/acetonitrile/TFA—about 40 wt % or more of material that has a molecular weight of about 5000 dalton or less, and about 10 wt % or more of material having a molecular weight of 1000 dalton or less. Generally, at least 10 wt %, or about 20 wt % or more of the keratinaceous material has a molecular weight of about 5000 dalton or higher.

Partly hydrolysed keratinaceous material for use in process step (iii) can be generally available keratinaceous meal or more generally referred to as Processed Animal Protein (PAP), like for example feather meal or hair meal, or more generally referred to as Feather hydrolyzed proteins and Porcine Bristle Meal or Porcine Bristle PAP or Porcine hydrolyzed proteins. This keratinaceous meal, or PAP is preferably produced with steam hydrolysation. As explained above, the process according to the present invention increases the flexibility in feedstock.

The keratinaceous material used in step (iii) of the process of the present invention still comprises the at least 17 amino acids, that make up the keratinaceous material, and this group of amino acids comprise very valuable amino acids like cysteine and tyrosine.

Although, for example, feather meal is useful as feed additive, a further hydrolysed (and thereby preferably soluble) peptide mixture obtained from keratinaceous material with the process according to the present invention has further added value, as the further hydrolysis increases the digestibility.

In another embodiment of the invention, the method for the production of highly digestible hydrolysed keratinaceous material comprises the steps of subjecting directly raw feathers, hair, wool, hoof or nails to a chemical hydrolysis step (iii) with acid or base to obtain a highly digestible hydrolysed material, and (iv) purifying the highly digestible hydrolysed material, preferably using any one of the preferences described herein.

The highly digestible keratinaceous material can be used as an ingredient in feed or food, for example to improve palatability and/or to improve flavor due to, among other, free amino acids, and the unique flavoring properties of cysteine. The amount of cysteine is about 2 wt % or more, more preferably about 3 wt % or more, even more preferably about 4 to 5 wt % or more. The wt % is expressed as relative to the total protein content.

The highly digestible keratinaceous material can equally be used, e.g. as dry powder or as a liquid concentrate, to feed young animals in their early phase of growth when their digestive capabilities are not yet (fully) developed or when faced to critical stages like for example the smoltification stage for young salmons. In shrimp feed, such hydrolysate can decrease stress and therefore reduce mortality rate. In general animal protein hydrolysate are recognized as being beneficial for the gut health and for activating hormones.

The use of the highly digestible keratinaceous material is in particular advantageous, because the absence of relatively high molecular weight molecules makes the hydrolysed keratinaceous material hypo- or even an-allergenic which can have beneficial nutritional effect on dogs and cats suffering from food intolerance and/or subject to allergenic problems.

In view of the further improved nutritional value of the keratinaceous material, the method of the present invention comprises (iii) a further chemical hydrolysation step to obtain a highly digestible keratinaceous material, and (iv) purifying the material.

Preferably, the chemical hydrolysis is performed with sufficient acid or base, during sufficient time and at a sufficient temperature that the hydrolysate comprises about 97% by weight of peptides about 10000 dalton or less, and more than 95% by weight of peptides with a molecular weight of about 5000 dalton or less. Further preferences are described as before.

The temperature at which the chemical hydrolysis is performed generally will be between about 60 and about 150° C. In one preferred embodiment, the temperature is between about 60° C. and about 100-110° C. (the reflux temperature of the mixture at atmospheric pressure). In another embodiment, pressurized equipment is used, and the temperature is between about 100 and 150° C. Preferably, the temperature will be below about 140° C., as higher temperatures require costly equipment. Higher temperatures increase the speed of the reaction, which is advantageous, although too harsh conditions may cause unwanted side reactions.

The time generally will be between half an hour to 12 hours, preferably between about 1 to 8 hours, like for example 1, 2 or 5 hours.

The amount of base or acid may vary as needed. Generally, an amount of about 30 wt % to about 200 wt % acid or base is used relative to the amount of keratinaceous material.

The reaction is performed preferably in water as a solvent, like for example 0.5 to 5 times the amount of water relative to the amount of keratinaceous material. More water can be used, but this is generally not preferred, as the water needs to be removed in order to obtain a dry highly digestible keratinaceous material. The resulting hydrolysate generally is a liquid, pourable material. It may be a true solution, emulsion or dispersion, and may be a viscous liquid. Hereinafter, the liquid phase will be denoted as solution, which comprises any liquid, water based fluid, and which may be an emulsion or dispersion.

The resulting hydrolysate is purified in order to remove the respective acid or base.

Purification can be done by one or more steps, optionally after neutralization of the respective base or acid, comprising evaporation, dialysis, electrolytic purification, filtration, membrane filtration and the like.

In a preferred embodiment, the purification is done by neutralizing the acid or base, and removing the salt formed by the neutralization. Neutralization can be done, by adding an acidic solution/dispersion to a base solution/dispersion, or adding a base solution/dispersion to an acid solution/dispersion.

In a particularly preferred embodiment, the purification is done while forming an insoluble salt, like for example a calcium sulphate salt, which can be removed with filtration or centrifugation. In this preferred embodiment, the hydrolysis can be performed with calcium oxide or calcium hydroxide as base, or with sulphuric acid as acid in the hydrolysis step.

In a preferred embodiment, a strong mineral acid is used in the hydrolysation step, as less side reactions occur with acid. In case a base is used, the hydrolysis is more likely to show de-amination side reactions. Suitable acids comprise sulphuric acid, hydrochloric acid and phosphoric acid.

Preferably, the following relative amounts are used in the hydrolysis: relative to 1 unit amount of keratinaceous material, between 0.2 and 5 equivalents of base or acid are used (preferably between 0.5 and 5 equivalents), while having between 0.5 and 3 equivalent amount of water. In a more preferred embodiment, the ratios are 1 to 0.5-2 to 0.5-2 (keratinaceous material:acid or base:water).

In a particularly preferred embodiment, sulphuric acid is used in the hydrolysis step, and calcium hydroxide (lime water) is used as neutralizing agent. The resulting salt can be removed with filtration or centrifugation to obtain a purified solution. Suitable equipment includes vacuum belt filters, worm centrifuges, horizontal or vertical scraper centrifuges and the like. Appropriate washing steps of the cake can be performed to increase the recovery of the hydrolyzed keratinaceous material and/or to reduce impurities in the cake.

The purified solution is preferably converted to a powder. Generally, the solution is concentrated to a solution with 30-60 wt % solids by evaporation, preferably at reduced pressure. Suitable equipment includes falling film, rising film or whipped film evaporators and the like. The concentrated solution can thereafter be dried while using suitable drying methods. Suitable drying techniques include a plurality of techniques, such as for example drum drying, spray drying and freeze drying.

The concentrated solution, which has about 10 wt % solids or more, preferably about 30 wt % solids or more, and more preferably has 40-55 wt % solids can also be used as such in feed application, as it can for example be sprayed on solid feed particles. The characteristics of the concentrated liquid with respect to in-vitro or in-vivo digestibility are preferably the same as for the dry powder product described below, calculated on dry matter.

In a preferred embodiment, a powder is obtained by spray drying a (concentrated) solution of the hydrolysate.

The dry highly digestible keratinaceous material preferably has an in vitro digestibility of about 95% or more, preferably about 98% or more (in both the ileal and pepsin digestibility test). The digestibility can be about 100%.

The dry highly digestible keratinaceous material preferably has an in vivo digestibility of the Total Nitrogen Matter of about 82% or more, preferably of about 85%, or more, and most preferable, about 90% or more as determined on cecectomized roosters.

The dry material preferably is in powder form and the particle size will depend of the type of spray dryer, or other dryer, and the re-agglomeration that can be performed. The particle size will also depend on the specifications of the customers. The material allows to obtain suitable particle sizes. A very pulverulent/dusty powder with a particle size of circa 50 μm (D50) can be made but is less preferred. A very suitable (fluid) powder, has been obtained while performing some agglomeration, and the D50 was 120-130 μm. The precise particle size is not essential. The material according to the invention can have a particle size distribution such that a d50 is between 30 and 1000 μm. Preferably the particles are all smaller than 1 mm, and preferably, the D90 (wherein 90 wt % of the particles is smaller than this size) is 0.5 mm. Such fine size powder is very suitable for fish feed when the fish is small like in the first 8 weeks.

Before or after drying, some amino acids may be added to the hydrolysate. In particular, it can be useful to add one or more of methionine, lysine, and tryptophan, as the amount of these amino acids is relatively low in keratinaceous material.

The highly digestible keratinaceous material in dry form or as a liquid concentrate can be incorporated into feather meal or other animal protein meals. Suitable amounts include a few percent, like between 0.2 to 5 wt %, preferably about 0.5 to 3 wt %, like for example about 1 wt % or about 2 wt %. The addition of the highly digestible keratinaceous material enhances the palatability and flavor of the feather meal, or of any other animal protein meal.

The dry highly digestible keratinaceous material can be packed in small bags, big-bags or other bulk containers. The liquid concentrated solution of the hydrolysate can be packed and shipped in any kind of Intermediate Bulk Container (IBC) or ISO Tank Containers or Flexitanks.

Measurement Methods

The following methods were used in the examples, and are suitable as methods to measure the parameters stated in the description and the claims:

Weight percentage (wt %) moisture: moist keratinaceous material is dried overnight in a vacuum stove at reduced pressure and with a siccative. The material is weighted before and after the drying step, and the amount of moisture is calculated using the initial measured weight as 100% while assuming that all the volatile material is water.

HPLC and Mw determination: Standard HPLC equipment can be used. The solvent for the keratinaceous material is MilliQ water, optionally with acetonitrile, and TFA in an amount of 0.1%. As a column, a Tosoh Bioscience Silica Column TSK G2000 SWXL 5 μm and Tosoh Bioscience Guard Column TSK-Gel SWXL 7 μm can be used, or comparable columns. The mobile phase is a trifluoroacetic acid 0.1 wt %, containing 15% acetonitrile (CH3CN). The recording is done with a UV detector at 214 nm. The column can be calibrated with a mixture of bacitracin, insulin, alpha-lacto-albumin, beta-lacto-globulin and tryptophan.

Solubility of the keratinaceous material is determined by dissolving 1 gram of keratinaceous material in 5 ml water of 20° C. The transparency of the liquid is determined by the human eye.

Pepsin digestibility is measured according to ISO 6655 (August 1997).

Ileal digestibility (also referred to as Boisen digestibility) is measured according to S. Boisen, 2007 ("In vitro analysis for determining standardized ileal digestibility of protein and amino acids in actual batches of feedstuffs and diets for pigs"; Livestock Science (2007) 309:182-185).

The in vivo digestibility of the Total Nitrogen Matter has been determined on cececctomized roosters, according to Johnson et al., 1998. "Effects of species raw material source, ash content, and processing temperature on amino acid digestibility of animal by-product meals by cececctomized roosters and ileally cannulated dogs" Journal of Animal Science; 76:1112-1122.

The amino acid analysis, lanthionine and de-carboxylated amino acids (like cadaverine, putrescine, or histamine) analysis are performed with standard HPLC methods.

Further modifications in addition to those described above may be made to the materials and methods described herein without departing from the spirit and scope of the invention. Accordingly, although specific embodiments have been described, these are examples only and are not limiting upon the scope of the invention.

EXAMPLES

Example 1-4

Feather from chicken was gathered. After washing the feathers, the amino acid composition was determined.

In a hydrolyser, working at 7 bar and saturated steam, feathers from chicken with a moisture content of 65 wt % were treated for 25 min. The partly hydrolysed fibre was brought to atmospheric pressure through a let-down valve, and the fibrous mass contained 55% of water.

The partly hydrolysed feather meal was dried in a number of different ways, with a classical disc dryer at 170° C. (8 bar pressure steam inside the disc), for about 1 hr, and for about 0.8 hr, a hot air dryer (fluidized bed dryer), and a disc dryer at 300 mbar pressure (abs). In the last mentioned drying method, the feather meal did not reach temperatures higher than about 70° C.

The throughput in the 4 plants was between 4 and 10 tonnes/hr.

TABLE 2

| characteristics of dried feather meal | | | | |
|---|---|---|---|---|
| | Example 1 | Example 2 | Example 3 | Example 4 |
| Process Characteristic | | | | |
| Hydrolyser Dryer | Batch Disc; 1 hr | Continuous Disc; 0.8 hr | Continuous Fluidized bed | Continuous Low temp disc (vacuum) |
| Meal quality | | | | |
| Pepsin digestibility | 54 | 64 | 74 | 85 |
| Ileal digestibility | 74 | 81 | 84 | 93 |
| Molecular weight | | | | |
| <5000 | 84 | 88 | 82 | 85 |
| <1000 | 57 | 42 | 48 | 56 |
| <500 | 45 | 27 | 29 | 42 |
| Percentage LAN | 2.3 | 2.2 | Nd | 1.3 |

The feather meal obtained after the drying step was further treated in a chemical hydrolysis step while using sulphuric acid. The sulphuric acid was used in an amount of 140% relative to the feather meal, with about 3 times the amount of water.

The hydrolysis was performed in a vessel, while stirring, for 5-7 hours at reflux temperature. After this step, lime water was slowly added, and calcium sulphate dihydrate precipitated. The calcium sulphate dihydrate was removed with filtration, and washed twice with water. The amount of organic material in the calcium sulphate dihydrate was less than 2 wt %.

The filtrate with the peptides was analysed with HPLC, and the analysis was as presented in table 3 (amounts in wt %):

TABLE 3

| Molecular weight | Example 1 | Example 2 | Example 3 | Example 4 |
| --- | --- | --- | --- | --- |
| Mw < 10000 | 100 | 100 | 100 | 100 |
| Mw < 5000 | 99 | 98 | 100 | 100 |
| Mw < 1000 | 85 | 75 | 98 | 95 |
| Mw < 500 | 60 | 50 | 83 | 80 |

The liquid hydrolysate was concentrated with low pressure evaporation till a concentration of about 45 wt % solids. Thereafter, the hydrolysate was spray dried in a pilot plant spray dryer. The molecular weight distribution of the keratinaceous material of the powder was measured (after dissolving the powder as a 1% solution in water), and approximately the same results were found as these presented in Table 3.

The dissolved powder obtained from example 4 was analysed for the amino acid composition, by common amino acid analysis. Results were obtained as given in Table 4:

TABLE 4

| Amino acid | Amount in hydrolysate Total amino acids (wt %) |
| --- | --- |
| Asp | 6.3 |
| Thr | 4.5 |
| Ser | 10.0 |
| Glu | 10.9 |
| Pro | 10.5 |
| Gly | 7.5 |
| Ala | 5.1 |
| Val | 8.5 |
| Cys | 4.7 |
| Met | 0.7 |
| Ile | 5.1 |
| Leu | 8.7 |
| Tyr | 2.2 |
| Phe | 5.2 |
| Lys | 2.0 |
| His | 0.9 |
| Arg | 7.2 |
| Total | 100% |

The table shows that all important amino acids were present, and that high quality feather meal as starting material has the additional advantage of producing hydrolysate with a small amount of anti-nutritional compounds. Furthermore, the results show that with the process of the present invention, a fully soluble keratinaceous material can be obtained with low amount of toxic materials like degraded amino acids. The keratinaceous material showed an ileal and pepsine digestibility of 100%. The amount of cadaverine was less than 100 ppm; the amount of lanthionine was 0.8 wt %, showing that little antinutritional compounds were present, and that virtually no degradation has occurred.

Example 5

In a batch hydrolyser, working at 7 bar and saturated steam, feathers from chicken with a moisture content of 65 wt % were treated for 25 min. The partly hydrolysed feather mass was brought to atmospheric pressure through a let-down valve, and the fibrous mass contained 65% of water.

The partly hydrolysed feather mass (the feather meal) was dried in a fluidized bed dryer. The inlet temperature of the hot air was 140° C. The feather meal did not reach temperatures higher than about 80° C., and drying till a moisture content of about 10 wt % took about 4 min.

The feather meal so obtained was stored for two month. Thereafter, 100 gram of meal was treated with a HCl solution at 80° C. for 3 hr. The HCl was neutralized with NaOH, and the salt was removed with electrodialysis over a membrane having a cut-off molecular weight of 60-80 dalton. Hence, virtually all mono-amino acids were retained in the product.

In an alternative process, the HCl was removed as described in U.S. Pat. No. 5,049,397, with evaporation of HCl, and further electrodialysis.

Example 6

A stirred mixture of 333 g chopped feathers with a moisture content of 70%, 27 g water and 143 g sulfuric acid was heated for 17.5 hours at reflux in a lab reactor. After cooling down to room temperature, lime water was slowly added and the mixture was stirred for 1 hour. The calcium sulphate dihydrate was removed with filtration. The protein content in the filtrate was 84.3 g (determined by Kjeldahl).

Example 7

A glass lined vessel, equipped with a stirring device and reflux condenser, was loaded with 100 kg feather meal, 228 kg water and 109 kg phosphoric acid. The mixture was heated to reflux and stirred at reflux temperature for 16 hours. After cooling down to room temperature, the mixture was transferred to another vessel containing 277 kg water and 96.1 kg calcium hydroxide. After stirring for 1 hour, dicalcium phosphate (calcium hydrogenphosphate di-hydrate) was removed with filtration and washed on the filter 3 times with 200 L water. The protein content in the combined filtrates was 65.0 kg (determined by Kjeldahl).

Example 8

A glass lined autoclave reactor was loaded with 15 kg feather meal, 34 kg water and 16.3 kg phosphoric acid. The mixture was heated at 150° C. in autogenic pressure conditions for 14 hours. After cooling down to room temperature, 41 kg water and 12.2 kg calcium hydroxide were added and the suspension was stirred further for 1 hour. After this step the dicalcium phosphate was removed with filtration. The protein content in the filtrate was 8.8 kg (determined by Kjeldahl).

Example 9

In a 100 L batch autoclave reactor, a mixture of 10 kg feather meal, 71 kg water and 1 kg calcium hydroxide was heated at 130° C. in autogenic pressure conditions for 6.5 hours. After cooling down to room temperature, the reaction medium was neutralized by adding sulfuric acid. After this step the calcium sulphate dihydrate was removed with filtration and washed 1 time on the filter with 10 L water. The protein content in the combined filtrates was 6.9 kg (determined by Kjeldahl).

Example 10

A glass lined vessel, equipped with a stirring device and reflux condenser, was loaded with 100 kg feather meal, 100 kg water and 100 kg sulfuric acid. The mixture was heated to reflux and stirred at reflux temperature for 6 hours. Next, the mixture was neutralized with lime water. After removal of the calcium sulphate dihydrate on a centrifuge, the hydrolysate was concentrated by low pressure evaporation. Spray drying of the resulting concentrate yielded 91 kg powder.

Analysis of this hydrolysate powder gave the following results: moisture 5%, ash 7%, digestibility 100% (Pepsin and Ileal). More than 99% of this keratinaceous material has a molecular weight of lower than 5000 dalton and about 97% of the material had a molecular weight lower than 1000 dalton. The in vivo digestibility of the Total Nitrogen Matter was 90% as measured on cecectomized roosters.

Further analysis revealed that the amount of lanthionine was 0.38%; biogenic amines were not increased significantly over those in the starting material. Hence, the increase in these side products because of the chemical hydrolysis step has been very limited.

The amino acid analysis (wt %) revealed the following:

| Amino acid | Amount in hydrolysate |
|---|---|
| Asp | 7.5 |
| Thr | 4.8 |
| Ser | 10.8 |
| Glu | 12.6 |
| Pro | 10.9 |
| Gly | 8.1 |
| Ala | 5.3 |
| Val | 8.0 |
| Cys | 3.3 |
| Met | 0.5 |
| Ile | 4.6 |
| Leu | 6.3 |
| Tyr | 1.6 |
| Phe | 4.9 |
| Lys | 2.4 |
| His | 0.8 |
| Arg | 7.8 |
| Total | 100% |

From this table, it appears that cysteine and leucine are substantially lower than in average feather meal. Maybe the starting feather meal was not of good quality. Nevertheless, still more than 3 wt % cysteine was present in the final hydrolysate. In a repeat experiment, the amount of cysteine was 4.1 wt %, and the amount of leucine 8.5 wt %. However, because of the different source of feather meal, the amount of lanthionine was 2.3%.

CONCLUSION

While the examples are illustrative only, the tests show that with the two-step hydrolysis process according to the present invention, including a chemical hydrolysis and purification step, highly valuable fully digestible amino acid composition from keratinaceous material can be obtained with little anti-nutritional or toxic compounds.

The ileal digestibility is determined via the following procedure, described in S. Boisen, Livestock Science (2007) 309:182-185:

Step 1: 1 g of finely ground material (<1 mm) is added to a 100 ml conical flask. 25 ml of phosphate buffer (0.1 M, pH, 6.0) is added and the mixture stirred. To the mixture is added 10 ml 0.2 M HCl, and pH is adjusted to pH 2 with 1 M HCl or a 1M NaOH solution. Then 1 ml of a freshly prepared pepsin solution, containing 10 mg pepsin (porcine, 2000 FIP-U g$^{-1}$) is added, as well as 0.5 ml chloramphenicol solution (0.5 g chloramphenicol per 100 ml ethanol). The flask is closed and stirred gently for 6 hours at 39° C.

Step 2: To the flask is added 10 ml of a phosphate buffer (0.2 M, pH 6.8), plus 5 ml 0.6 M NaOH solution. The pH is adjusted to 6.8 with 1 M HCl or 1 M NaOH solution. The mixture is then mixed with 1 ml of a freshly prepared pancreatin solution containing 50 mg pancreatin (porcine, grade IV). The flask is closed and stirred gently for 18 h at 39° C.

5 ml of 20% sulphosalicylic acid is added, and after 30 min the undigested residues are collected in a filtration unit, by using dried and pre-weight glass filter crucibles containing about 0.5 g Celite as filter aid. The filter is washed with 10 ml ethanol, and 10 ml acetone, and the undigested residues are dried overnight at 80° C. The in vitro digestibility of dry matter is calculated from the difference between dry matter in the sample and the undigested residue after correction for dry matter obtained in a blank sample.

The pepsin digestibility is determined via the following procedure, described in specification ISO 6655 (August 1997):

Step 1: about 2 g of material is weighed and added to a volumetric flask of 500 ml. 450 ml of pepsin solution (0.2 g pepsin in 1 L 0.075 M HCl), previously heated to 40° C., is added and the flask is stirred. The pH is verified to be below 1.7. The flask is placed in a 40° C. bath for 48 h, and agitated at the 8, 24 and 32 h mark. After 48 hours, 15 ml of 7.5 M HCl solution is added to the mixture, the flask is cooled to 20° C. and agitated. The mixture is filtered over a paper filter.

Step 2: The nitrogen content of the filtrate is determined via the Kjeldahl method.

Step 3: The nitrogen content of the filter residue is determined via the Kjeldahl method.

The pepsin digestibility is the nitrogen content of the filtrate divided by the total nitrogen content.

What is claimed is:

1. A method for the production of a digestible hydrolysed material, comprising the steps of
   (i) partly hydrolysing a keratinaceous material in the presence of water with heat and pressure wherein the hydrolysis reaction is performed with only water/steam as the active reagent at a pressure of 4 bar absolute or higher, to obtain partly hydrolysed keratinaceous material which comprises—when dissolved in water/acetonitrile/TFA—about 40 wt % or more of material that has a molecular weight of about 5000 dalton or less, and about 20 wt % or more of material having a molecular weight of about 5000 dalton or higher, and
   (ii) subjecting the partly hydrolysed keratinaceous material to a chemical hydrolysis step with an strong mineral acid to obtain the digestible hydrolysed material, and
   (iii) purifying the digestible hydrolysed material,
   wherein the digestible hydrolysed material has 90% by weight or more of material of a molecular weight of 1000 dalton or lower, and an in vitro ileal digestibility of 98% or more, and an in vitro pepsin digestibility of 98% or more.

2. The method according to claim 1, wherein in step (i) the keratinaceous material is hydrolysed at a pressure between 4 bar absolute and about 15 bar absolute, during about 5 to about 240 min.

3. A method for the production of a digestible hydrolysed material comprising the steps of subjecting a partly hydrolysed, partly insoluble keratinaceous material to a further chemical hydrolysis step, wherein the partly hydrolysed, partly insoluble keratinaceous material comprises—when dissolved in water/acetonitrile/TFA—about 40 wt % or more of material that has a molecular weight of about 5000 dalton or less, and about 20 wt % or more of material having a molecular weight of about 5000 dalton or higher, obtained from thermal and pressure hydrolysis, wherein the hydrolysis reaction is performed with only water/steam as the active reagent at a pressure of 4 bar absolute or higher, and wherein the further chemical hydrolysis step comprises chemical hydrolysis with an strong mineral acid to obtain the digestible hydrolysed material, and purifying the digestible hydrolysed material wherein the digestible material has 90% by weight or more of material of a molecular weight of 1000 dalton or lower and an in vitro ileal digestibility of 98% or more, and an in vitro pepsin digestibility of 98% or more.

4. A method for the production of a digestible hydrolysed keratinaceous material comprising subjecting a partly hydrolysed keratinaceous material with a moisture content of about 10 wt % or less to a chemical hydrolysis step, wherein the partly hydrolysed keratinaceous material is a keratinaceous meal, wherein the partly hydrolysed keratinaceous material comprises—when dissolved in water/acetonitrile/TFA—about 40 wt % or more of material that has a molecular weight of about 5000 dalton or less, and about 20 wt % or more of material having a molecular weight of about 5000 dalton or higher, wherein the chemical hydrolysis step comprises chemical hydrolysis with a strong mineral acid to achieve the digestible hydrolysed keratinaceous material, and purifying the digestible hydrolysed keratinaceous material wherein the digestible material has 90% by weight or more of material of a molecular weight of 1000 dalton or lower and an in vitro ileal digestibility of 98% or more, and an in vitro pepsin digestibility of 98% or more.

5. The method according to claim 1, wherein the strong mineral acid is sulphuric acid.

6. The method according to claim 5, wherein the purification (iii) of the digestible hydrolysed material is performed while forming a salt by neutralisation and separating the salt from the digestible hydrolysed material, wherein the salt is calcium sulphate dihydrate, which is removed.

7. The method according to claim 1, wherein a solution comprising the digestible hydrolysed material is converted to a concentrated solution comprising about 30-60 wt % solids.

8. The method according to claim 1, wherein a solution comprising the digestible hydrolysed material is converted to a solid.

9. A digestible hydrolysed keratinaceous material, obtainable with the method of claim 1, wherein the digestible hydrolysed keratinaceous material has an amino acid composition reflecting the amino acid composition of the keratinaceous material, wherein an amount of de-carboxylated amino acids is less than about 1000 ppm, and wherein the digestible keratinaceous material has 90% by weight or more of material of a molecular weight of 1000 dalton or lower and an in vitro ileal digestibility of 98% or more, and an in vitro pepsin digestibility of 98% or more.

10. The digestible hydrolysed keratinaceous material according to claim 9, wherein the digestible hydrolysed keratinaceous material contains lanthionine in an amount of about 2.0 wt % or less.

11. The digestible hydrolysed keratinaceous material according to claim 9, wherein the digestible hydrolysed keratinaceous material has an in vivo digestibility of the Total Nitrogen Matter of about 82% or more, as determined on cecectomized roosters.

12. The method according to claim 1, wherein step (i) further comprises drying the partly hydrolysed keratinaceous material and wherein step (ii) comprises subjecting the dried partly keratinaceous hydrolysed material to the chemical hydrolysis step with a strong mineral acid to obtain the digestible hydrolysed material.

13. A feed or feed additive comprising the digestible hydrolysed material obtained according to claim 1, wherein the digestible hydrolysed material has an amino acid composition reflecting the amino acid composition of the keratinaceous material wherein the deviation in amino acid composition of the digestible hydrolysed material and the keratinaceous material is less than 20% in the amino acids, and/or a deviation in an amount absolute of less than 0.4 wt % in the amino acids, whereby up to 3 amino acids deviate to a maximum of 40% or 2 wt %, and wherein an amount of de-carboxylated amino acids is less than about 1000 ppm.

14. The method according to claim 12, wherein the drying in step (i) is performed at a temperature below 80° C.

\* \* \* \* \*